United States Patent
Schwartz et al.

[11] Patent Number: 5,336,756
[45] Date of Patent: Aug. 9, 1994

[54] PROCESS FOR CRYSTALLINE CYCLIC LIPOPEPTIDES

[75] Inventors: Robert E. Schwartz, Westfield, N.J.; August J. Kempf, Staten Island, N.Y.; David J. Mathre, Edison, N.J.

[73] Assignee: Merck & Co., Inc., Rahway, N.J.

[21] Appl. No.: 750,379

[22] Filed: Aug. 27, 1991

Related U.S. Application Data

[63] Continuation-in-part of Ser. No. 692,073, May 1, 1991, abandoned.

[51] Int. Cl.$^5$ .............................. C07K 1/14; C07K 7/54
[52] U.S. Cl. ................................... 530/317; 530/344
[58] Field of Search ............... 530/300, 317, 322, 345, 530/344; 514/11

[56] References Cited

U.S. PATENT DOCUMENTS 5,198,421  3/1993  Chen et al. ........................ 435/71.1
5,202,309  4/1993  Schwartz et al. .................... 514/11

FOREIGN PATENT DOCUMENTS 0405997  1/0291  European Pat. Off. .

OTHER PUBLICATIONS

Weissberger, Technique of Org. Chem., Part 1, Separation & Purif. (Intersci. Pub. Inc. New York), 1956, pp. 548–561.

*Primary Examiner*—Jeffrey E. Russel
*Attorney, Agent, or Firm*—Elliott Korsen; Mark R. Daniel

[57] ABSTRACT

A process for obtaining a compound of the formula

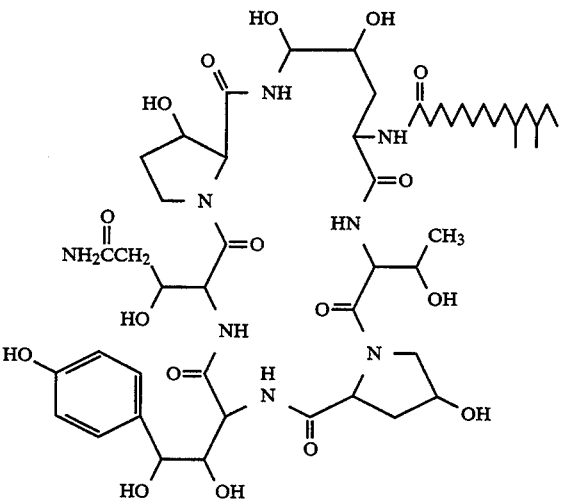

in crystalline form by solubilizing the compound in warm aqueous n-propanol and then allowing the solution to stand at ambient temperature until crystal formation is substantially complete is described. The crystalline compound obtained thereby is also described.

3 Claims, 1 Drawing Sheet

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 6 amino acids
( B ) TYPE: amino acid
( C ) STRANDEDNESS: single
( D ) TOPOLOGY: circular ( i i ) MOLECULE TYPE: peptide ( x i ) SEQUENCE DESCRIPTION: SEQ ID NO:1:

Xaa Thr Xaa Xaa Xaa Xaa
1           5

PROCESS FOR CRYSTALLINE CYCLIC LIPOPEPTIDES

This is a continuation-in-part of application Ser. No. 07/692,073 filed May 1, 1991, now abandoned.

This invention is directed to a process for obtaining certain cyclic lipopeptides in crystalline form and to the crystalline products obtained thereby.

BACKGROUND OF THE INVENTION

Cyclic lipopeptides, generally hexapeptides, have been obtained as secondary metabolites on the cultivation of certain fungi and have been reported to be antifungal agents, especially against Candida species. In addition, semi-synthetic cyclic lipopeptides obtained by deacylation of the lipophilic side chain of a natural cyclic lipopeptide and then reacylating to obtain novel unnatural cyclic lipopeptides have also been reported to be useful against Candida species.

These compounds are oftentimes referred to in the art as echinocandin type compounds. These compounds are reported as amorphous solids or as films. No cyclic lipopeptide has been obtained in crystalline form. For ultimate utilization in therapy, it is desirable that the compound be of sufficient purity to be in crystalline form.

A particularly useful cyclic lipopeptide being highly effective against Pneumocystis carinii, the causative agent of pneumocystis pneumonia as well as having superior properties as an antifungal agent, is a compound (seq. ID No: 1) having the following formula (I):

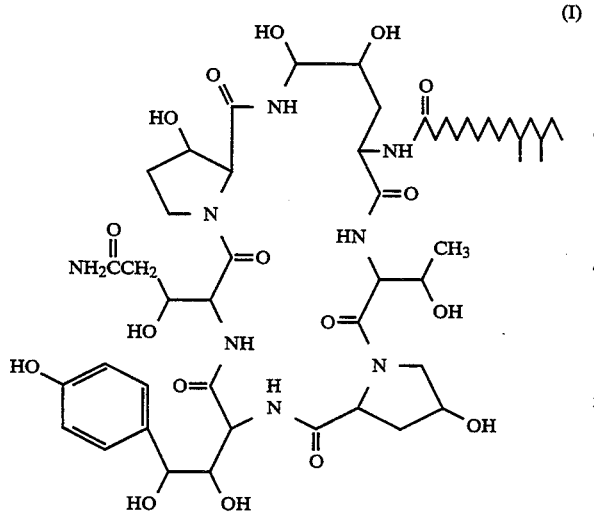

The compound of formula (I) (hereinafter also Compound I) is the subject of copending application Ser. Nos. 07/492,025 filed on Mar. 12, 1990, and 07/492,026, filed on Mar. 12, 1990, now U.S. Pat. No. 5,021,341, issued on Jun. 4, 1991 and may be named 1-[4,5-dihydroxy-$N^2$-(10,12-dimethyl-1-oxotetradecyl) ornithine]-5-(3-hydroxy-glutamine)-6-(3-hydrory-proline)echinocandin B. The preferred stereoisomer is thought to be: 1-[4R,5R-dihydroxy $N^2$-(10,12-dimethyl-1-oxotetradecyl)-L-ornithine]-5-(3R-hydroxy-L-glutamine)-6-[3S-hydroxy-L-proline]echinocandin B. This compound also had not been obtained in crystalline form.

BRIEF DESCRIPTION OF THE DRAWING

The X-ray structure and stereoisomeric configuration of the compound has now been obtained as seen in FIG. 1 and as hereinafter described.

DETAILED DESCRIPTION

Figure 1:
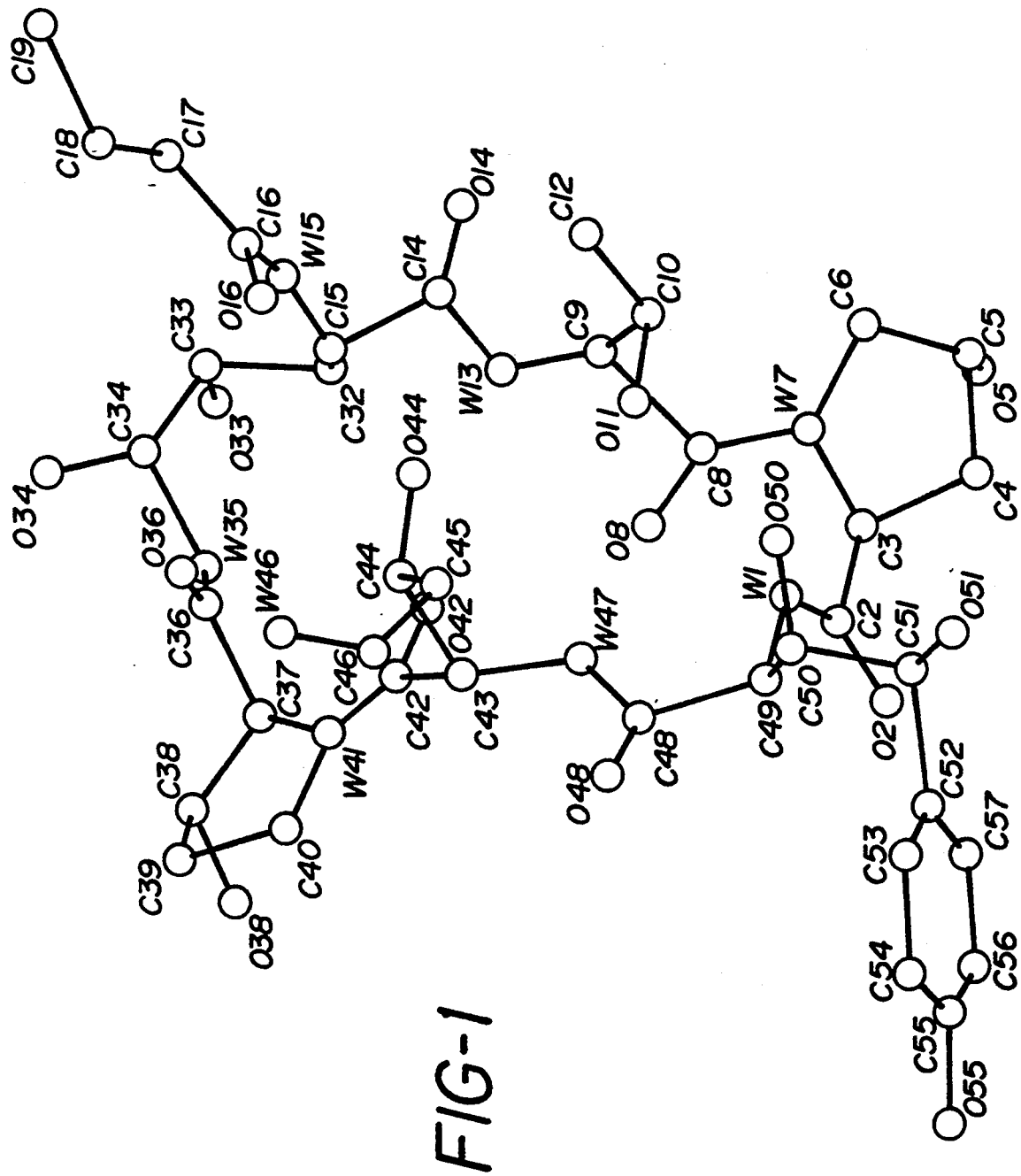

As disclosed in the above-identified applications, the superior properties of this compound as a therapeutic agent in the treatment of mycotic infections were demonstrated against Candida albicans, Candida tropicalis and Candida parapsilosis in a standard microbroth dilution assay with 1% dextrose. The results showed a minimum fungicidal concentration in the range of 0.25 to 1.0 µg/ml against several strains of C. albicans, 20 µg/ml, against C. tropicalis and 8.0 µg/ml against C. parapsilosis.

The efficacy of the compound against Pneumocystis carinii infections was demonstrated in a representative study against mice which had been immunosuppressed for six weeks to develop P. carinii infections, and in which study, the mice were injected intraperitoneally twice daily at a dose of 0.5 mg/kg for two weeks. It was found that there was an 81 percent reduction in the number of cysts of the treated animals as compared to control animals.

According to the present invention, it has been discovered that certain echinocandin type compounds, especially the compound of formula (I), may be obtained in crystalline form when aqueous n-propanol is employed as the crystallizing solvent. n-Propanol is essential as the primary solvent for a practicable process. Other alkanols such as ethanol, methanol, isopropanol and butanol are not useful for facilely producing a crystalline product. Moreover, it is critical and essential for crystallization to take place that there be water. When there is no water or there is too little water, there is gel formation rather than crystallization. Also, when the amount of water exceeds a certain amount, there is little or no formation of crystals. The source of water could arise from the atmosphere. Thus, for example, a water-free n-propanol, as in a freshly opened bottle assaying 0.12 percent water by Karl Fischer, after standing overnight was found to assay 2.29 percent water. Generally, an amount of water of from about 2 to about 8 percent of the n-propanol is suitable for crystallization. A preferred range is from about 3 to 5 percent, most preferably from about 3.5 to 4 percent.

In carrying out the crystallization, the cyclic lipopeptide compound is dissolved in aqueous n-propanol, employing an amount of from about 25 to 200 milligrams of the lipopeptide per milliliter of n-propanol/$H_2O$. The dissolution is carried out with warming, preferably in the temperature range of about 55° to 65° C. After all or substantially all of the material is dissolved, the solution is filtered and aged at ambient temperature for from about 12 to 20 hours to form crystals of the cyclic lipopeptide compound of formula (I) of greater than 90 percent purity. If desired, the time may be shortened somewhat by cooling.

Crystallization appears to occur with the association of about six moles of water per mole of the compound.

The following examples illustrate the invention but are not to be construed as limiting.

EXAMPLE 1

50 milligrams of a sample of a compound of formula (I) in amorphous form was dissolved in a milliliter of 60°

C. n-propanol; a gel formed on cooling. The sample was divided into two portions, placed in tubes, the tubes heated to 60° C., then sealed and thereafter allowed to stand at room temperature for 19 days. One of the tubes which apparently sustained a break in the seal and exposure to the atmosphere as evidenced by diminished volume, had small but birefringent crystals.

The seal of the second sample then was intentionally broken, the solution opened to the atmosphere and allowed to stand whereupon good quality crystals were found to form.

EXAMPLE 2

245 milligrams of an amorphous sample of the compound of formula (I) was dissolved by heating in 4.9 milliliters of fresh n-propanol in a 60° C. water bath. The almost completely dissolved solution was filtered through a glass wool plug and subdivided into 1 milliliter aliquots. To the aliquots were added varying amounts of water, the containers closed, allowed to stand at room temperature and observed. After 16 hours, the results were as follows (Table I).

TABLE I

| Percent Water | Appearance |
| --- | --- |
| 0 | Milky; no crystals |
| ½ | Milky; no crystals |
| 1 | Very few crystals |
| 2 | Small good crystals |
| 5 | Good crystals |

EXAMPLE 3

338 milligrams of the compound of formula (I) and 6 milliliters of n-propanol were heated in a 60° C. water bath and the resulting mixture filtered through glass wool and to the filtrate was added 300 microliters of water to obtain a 5 percent aqueous propanol solution. The mixture was allowed to stand overnight in a closed container. Very good crystals were found to have formed. The crystals were dried and after drying was found to amount to 151 milligrams or 45 percent yield. An HPLC analysis of the harvested crystals showed that two impurities present in the starting material had been decreased by 30 percent.

Karl Fisher analysis on the crystals indicated the presence of 6 moles of water.

EXAMPLE 4

101 milligrams of Compound I was added to 2 milliliters of 95/5 n-propanol/water and the mixture heated in a 60° C. water bath. Not all the material dissolved. Another 60 microliters of water was added to obtain a 7.8 percent water solution. Substantially all the solid dissolved. The mixture was filtered through glass wool and left at room temperature in a closed container overnight. Rod shaped crystals with hexagonal faces were found to have formed.

EXAMPLE 5

10.0 grams of Compound I was dissolved in 90 milliliters of n-propanol (KF =1.2 mg/ml) by heating at reflux temperature. The mixture was filtered hot and divided into 10 equal portions, each portion containing 5.0 mg/mL. Water was added to each portion ranging from 2 percent water to 7 percent water. Within 15 minutes (C), (D) and (E) in Table I formed a seed bed. These were reheated to dissolve the crystals and all solutions allowed to stand for about 48 hours, whereupon it was found that crystals had formed. The solution was decanted and the crystals washed with n-propanol and dried under vaccuum (45 cm) for 12 hours. The crystals were assayed by HPLC for percent of Compound I. The results are summarized in the following table (Table II):

TABLE II

| | Solution Volume (ml) | Volume $H_2O$ Added (μl) | Weight Isolated Compound (grams) |
| --- | --- | --- | --- |
| (A) | 10.0 | 300 | 0.754 |
| (B) | 10.0 | 350 | 0.852 |
| (C) | 10.0 | 400 | 0.841 |
| (D) | 10.0 | 450 | 0.700 |
| (E) | 10.0 | 500 | 0.715 |
| (F) | 10.0 | 550 | 0.677 |
| (G) | 10.0 | 600 | 0.588 |
| (H) | 10.0 | 650 | 0.533 |
| (I) | 10.0 | 700 | 0.473 |

EXAMPLE 6

In operations carried out in the manner described in Example 4 but including a lower concentration of water, determinations were made on the purity of the crystals formed. The results are found in Table III.

TABLE III

| Percent Water | Percent Purity of Crystals |
| --- | --- |
| 2.0 | 91.7 |
| 3.0 | 92.1 |
| 3.5 | 92.6 |
| 4.0 | 92.4 |
| 4.5 | 90.9 |
| 5.0 | 90.7 |
| 5.5 | 92.4 |
| 6.0 | 90.6 |
| 6.5 | 92.9 |
| 7.0 | 92.9 |

EXAMPLE 7

50 milligrams of an amorphous sample of Compound I was dissolved in one milliliter of 95% n-propanol/5% water by heating in a water bath to 60° C. The sample was allowed to cool to room temperature overnight, at which time small crystals had formed.

The sample was recrystallized by reheating to 60° to redissolve the crystals and again allowing the solution to cool to room temperature resulting in the formation of larger crystals. This process was repeated until a crystal sufficiently large for a single crystal X-ray analysis was obtained.

X-ray crystallographic analysis was carried out on a RIGAKU AFC5 diffractometer and the structure of Compound I was determined as indicated in FIG. 1. This may also be seen in the following alternative representation:

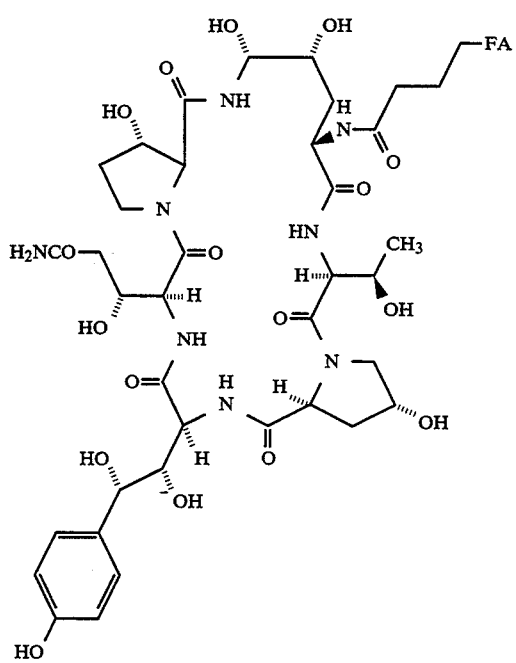

Preparation of Starting Materials

The starting material used in the working examples were obtained in the following way:

Seed cultures were first prepared in several stages from P34-2 medium of the following composition:

|  | per/liter |
| --- | --- |
| Corn steep liquor | 5 g |
| D-mannitol | 10 g |
| Glucose monohydrate | 10 g |
| PHARMAMEDIA* | 20 g |
| $KH_2PO_4$ | 9 g |
| $FeSO_4.7H_2O$ | 10 mg |
| $MnSO_4.4H_2O$ | 10 mg |
| $CuCl_2.2H_2O$ | 0.25 mg |
| $CaCl_2.2H_2O$ | 1 mg |
| $H_3BO_3$ | 0.56 mg |
| $(NH_4)_6Mo_7O_{24}.H_2O$ | 0.19 mg |
| $ZnSO_4.7H_2O$ | 2 mg |

*nonhydrolyzed globular protein Buckeye Oilseed Products

As the initial step, 54 milliliters of P34-2 medium was inoculated with *Zalerion arboricol* MF5533 ATCC 74030 and the inoculated medium was incubated with shaking at 220 rpm at 25° C. for four days. A twenty-milliliter sample of this seed medium was used to inoculate each of four 2-liter flasks containing 500 milliliters of P34-2 medium and the inoculated medium incubated at 25° C. for four days at 220 rpm. The flask contents were then pooled and used to inoculate a 300-liter seed fermenter containing 180 liters of P34-2 medium and 2 milliliters/liter of polypropylene glycol P-2000 to reduce foaming. The fermenter was operated for six days at a temperature of 25° C., an air flow of 90 liters per minutes, a pressure of 0.7 kg/cm² gauge, and an agitator speed of 200 rpm. A 25 liter sample of this seed then was used to inoculate an 800 liter seed fermenter containing 475 liters of P34-2 medium and 2 milliliter/liter of P-2000 and cultivated for four days at 25° C., air flow of 250 liter/minute, a pressure of 0.7 kg/cm² gauge and agitator speed of 150 rpm.

425 liters of the seed broth thus prepared was inoculated into 13,700 liters of TG 106 medium of the following composition in a 19,000 liter production fermenter.

|  | per liter |
| --- | --- |
| D-Mannitol | 100 g |
| NZ-Amine type E* | 33 g |
| Fidco 8005 yeast extract | 10 g |
| $(NH_4)_2SO_4$ | 5 g |
| $KH_2PO_4$ | 9 g |
| P-2000 | 2 ml |

*Casein hydrolysate, Sheffield Products, Kraft, Inc.

Fermentation of the mixture was carried out at a temperature of 25° C., air flow of 6300 liters/minute, a pressure of 0.7 kg/cm² gauge and agitator speed of 80 rpm. The pH was allowed to decrease from an initial value of 6.0 to 5.5 and then maintained at 5.5±0.2 using sodium hydroxide or sulfuric acid. The cultivation was continued for twelve days, after which time the broth was harvested for product isolation.

The broth from the foregoing cultivation was first extracted with an equal volume of methanol. The methanol-broth was clarified using a liquid-solid separator (centrifuge) to obtain clarified liquid as first extract and solid. The extraction-clarification was repeated. The extracts were combined and the water content adjusted to about 50 percent. The resulting solution was passed through an DIAION SP-207 (brominated styrene-divinylbenzene copolymer adsorption column, Mitsubishi) to adsorb Compound I and the column washed with aqueous methanol.

Thereafter Compound I was recovered with 100 percent methanol. The methanol fractions containing Compound I was adjusted to about 50 percent water and the solution passed through a DIAION HP-20 (styrene-divinylbenzene copolymer adsorption column, Mitsubishi) and the process repeated.

The water content of the methanol containing Compound I was adjusted to 50 percent and the aqueous methanol solution intimately mixed with an equal volume of 1:1 isopropyl acetate/hexanes and the two-liquid phases thereafter separated. The aqueous methanol layer was passed through a column of SP-207, the column washed with aqueous methanol. Compound I then was eluted with 100 percent methanol and the eluate vacuum concentrated to minimum volume and the solvent composition adjusted to about 75:20:5 ethyl acetate/methanol/water.

The feed thus prepared was passed through a silica gel column and Compound I eluted with 85:10:5 ethyl acetate/methanol/water. The fractions showing 85 percent or greater area purity by HPLC were combined, vacuum concentrated to remove ethyl acetate and the contentrate adjusted to 50 percent aqueous methanol. The latter was passed through a HP-20 column in the manner previously described; the eluate was concentrated and Compound I precipitated with acetonitrile, recovered by vacuum filtration and then dried.

*Z. arboricola* MF5533 ATCC 74030 is disclosed and claimed in copending application Ser. No. 630,457, filed Dec. 19, 1990. Briefly it may be obtained by (a) inoculating a frozen vegetative mycelium of *Z. arboricola* ATCC 20957 (disclosed and claimed in copending application Ser. No. 492,024) into KF seed medium: corn steep liquor, 5 g/l; tomato paste, 40 g/l; oat flour, 10 g/l; glucose, 10 g/l; $FeSO_4 \cdot 7H_2O$, 10 mg/l; $MnSO_4 \cdot 4H_2O$, 10 mg/l; $CuCl_2 \cdot 2H_2O$, 0.25 mg/l; $CaCl_2 \cdot 2H_2O$, 1 mg/l;

$H_3BO_3$, 0.56 mg/l; $(NH_4)_6Mo_7O_{24} \cdot H_2O$, 0.19 mg/l; $ZnSO_4 \cdot 7H_2O$, 2 mg/l; (b) adding to the medium N-methyl-N'-nitro-N-nitrosoguanidine (NTG) and cultivating, (c) plating a portion of the growth on potato dextrose agar and incubating for 14 days at 25° C. to obtain spores, then (d) harvesting the spores, diluting with sterile saline, plating on potato dextrose agar and incubating for 7 days for colony formation, and (e) transferring the separate colonies to slants of potato and incubating for 14 days at 25° C.

The starting material also may be prepared by methods described in copending application Ser. Nos. 07/492,025 and 07/492,026, now U.S. Pat. No. 5,021,341, Jun. 4, 1991.

What is claimed is:

1. A process for obtaining in crystalline form a compound (SEQ ID No. 1) having the formula:

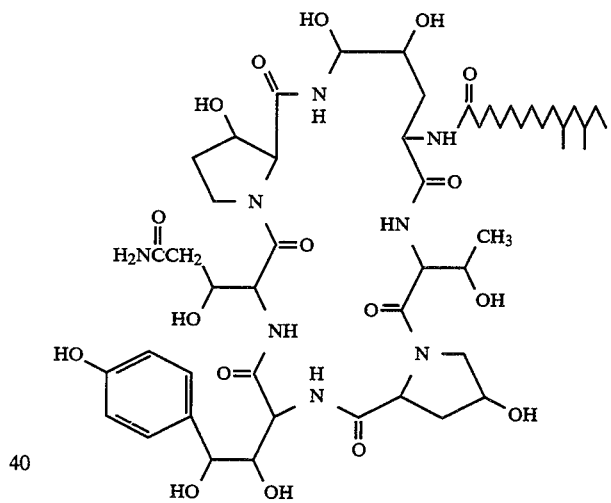

which comprises
(1) solubilizing the compound in aqueous n-propanol at about 55° to 65° C. and
(2) allowing the solution to stand at ambient temperature until crystal formation is substantially complete.

2. A process according to claim 1 wherein the aqueous n-propanol is n-propanol with a water content of from about 2 to 8 percent based upon volume.

3. A process according to claim 1 wherein the aqueous n-propanol is n-propanol with a water content of from about 3.5 to 4 percent based upon volume.

* * * * *